(12) United States Patent
Irudayaraj et al.

(10) Patent No.: US 9,968,692 B2
(45) Date of Patent: May 15, 2018

(54) NANOBUBBLES

(71) Applicant: Purdue Research Foundation, West Lafayette, IN (US)

(72) Inventors: Joseph Irudayaraj, West Lafayette, IN (US); Pushpak Bhandari, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days. days.

(21) Appl. No.: 14/873,208

(22) Filed: Oct. 2, 2015

(65) Prior Publication Data
US 2016/0166716 A1 Jun. 16, 2016

Related U.S. Application Data

(60) Provisional application No. 62/058,793, filed on Oct. 2, 2014, provisional application No. 62/075,496, filed on Nov. 5, 2014, provisional application No. 62/147,267, filed on Apr. 14, 2015.

(51) Int. Cl.
| | |
|---|---|
| A61K 49/22 | (2006.01) |
| A61K 31/337 | (2006.01) |
| A61K 33/00 | (2006.01) |
| A61K 41/00 | (2006.01) |
| A61K 9/51 | (2006.01) |
| A61K 9/00 | (2006.01) |
| C12N 15/115 | (2010.01) |

(52) U.S. Cl.
CPC .......... *A61K 49/223* (2013.01); *A61K 9/0009* (2013.01); *A61K 9/5161* (2013.01); *A61K 31/337* (2013.01); *A61K 33/00* (2013.01); *A61K 41/0028* (2013.01); *C12N 15/115* (2013.01); *C12N 2310/16* (2013.01); *C12N 2320/32* (2013.01)

(58) Field of Classification Search
None
See application file for complete search history.

(56) References Cited

U.S. PATENT DOCUMENTS

| 7,338,451 B2 * | 3/2008 | Tsuzuki | G01S 7/52038 600/458 |
|---|---|---|---|
| 2007/0059248 A1 * | 3/2007 | Unger | A61K 49/223 424/9.52 |
| 2013/0041311 A1 * | 2/2013 | Kohane | A61K 9/0009 604/22 |

OTHER PUBLICATIONS

Wu, H., et al., "Acoustic Characterization and Pharamacokinetic Analyses of New Nanobubble Ultrasound Contrast Agents", Ultrasound. Med. Biol., 2013, pp. 2137-2146.*
Iannuccelli, V., et al., "Effect of the loading method on the drug release from cross-linked carboxymethylcellulose beads", J. Contr. Release, 1993, pp. 13-20.*
Sharpiro, M. G., et al., Biogenic gas nanostructures as ultrasonic molecular reporters. Nature Nanotechnology, 2014, 9, 311-316.
Goldberg, A.D., et al., Epigenetics: A Landscape Takes Shape. Cell, 2007, 128, 635-638.
Chen, J., et al., Fluorescence Lifetime Cross Correlation Spectroscopy Resolves EGFR and Antagonist Interaction in Live Cells. Anal. Chem. 2010, 82, 6415-6421.
Gonzalo, S., Epigenetic alterations in aging. J Appl Physiol 109: 586-597, 2010.
Formenti, F., et al., Regulation of human metabolism by hypoxiainducible factor. Proc. Natl. Acad. Sci. USA, 2010, 107, 12722-12727.
Maxwell, P.H., et al. The tumour suppressor proteinVHL targets hypoxia-inducible factors for oxygen-dependent proteolysis. Nature, 1999, 399, 271-275.
Wang, G.L., et al., Hypoxia-Inducible Factor 1 is a Basic-Helix-Loop-Helix-PAS Heterodimer Regulated by Cellular O2 Tension. Proc. Natl. Acad. Sci. USA, 1995, 92, 5510-5514.
Ema, M. et al., A novel bHLH-PAS factor with close sequence similarity to hypoxia-inducible factor 1a regulates the VEGF expression and is potentially involved in lung and vascular development. Proc. Natl. Acad. Sci. USA, vol. 94, pp. 4273-4278, Apr. 1997.
Tsakalozou, E., et al., Combination Effects of Docetaxel and Doxorubicin in Hormone-Refractory Prostate Cancer Cells. Biochemistry Research International, vol. 2012, Article ID 832059, 10 pages, doi:10.1155/2012/832059.
Chen, J., et al., Quantitative Investigation of Compartmentalized Dynamics of ErbB2 Targeting Gold Nanorods in Live Sells by Single Molecule Spectroscopy. ACS Nano 2009, vol. 3, 4071-4079.
Mackler, N.J., et al., Drug Insight: use of docetaxel in prostate and urothelial cancers. Nature Clinical Practice Urology, 2005, vol. 2, 92-100.
Zhang, X.H., et al., Nanobubbles at the Interface between Water and a Hydrophobic Solid. Langmuir 2008, 24, 4756-4764.
Habich, A., et al., Do Stable Nanobubbles Exist in Mixtures of Organic Solvents and Water? J. Phys. Chem. B 2010, 114, 6962-6967.
Zhao Y., et al., Potential and problems in ultrasound-responsive drug delivery systems. International Journal of Nanomedicine 2013:8 1621-1633.
Horie, S. et al., Development of Localized Gene Delivery Using a Dual-Intensity Ultrasound System in the Bladder. Ultrasound in Med. & Biol., vol. 36, No. 11, pp. 1867-1875, 2010.
Fan, X., et al., Experimental investigation of the penetration of ultrasound nanobubbles in a gastric cancer xenograft. Nanotechnology 24 (2013) 325102 (10pp) doi:10.1088/0957-4484/24/32/325102.

(Continued)

*Primary Examiner* — Michael G Hartley
*Assistant Examiner* — Lance W Rider
(74) *Attorney, Agent, or Firm* — Purdue Research Foundation; Yonghao Hou

(57) ABSTRACT

The present invention provides a nanobubble comprising a continuous outer shell, the outer shell comprising a cross-linked polymeric material, an inner wall of the continuous outer shell and a hollow core within the continuous outer shell. The nanobubble may be less than 250 nm in diameter. In a further aspect of the invention, the cross-linked polymeric material is a cellulose-based material.

13 Claims, 13 Drawing Sheets

(56) References Cited

OTHER PUBLICATIONS

Yin, T., et al., Tumor-penetrating codelivery of siRNA and paclitaxel with ultrasound-responsive nanobubbles hetero-assembled from polymeric micelles and liposomes. Biomaterials 35 (2014) 5932-5943.

Huang, H., et al., A Multitheragnostic Nanobubble System to Induce Blood-Brain Barrier Disruption with Magnetically Guided Focused Ultrasound. Adv. Mater 2015, 27, 655-661.

Rapoport, N.Y., et al., Controlled and targeted tumor chemotherapy by ultrasound-activated nanoemulsions/microbubbles. Journal of Controlled Release 138 (2009) 268-276.

Mohan, P., et al., Doxorubicin as a Molecular Nanotheranostic Agent: Effect of Doxorubicin Encapsulation in Micelles or Nanoemulsions on the Ultrasound-Mediated Intracellular Delivery and Nuclear Trafficking. Molecular Pharmaceutics, 2010, vol. 7, 1959-1973.

Wang, C., et al., Gold Nanorod/Fe3O4 Nanoparticle "Nano-Pearl-Necklaces" for Simultaneous Targeting, Dual-Mode Imaging, and Photothermal Ablation of Cancer Cells. Angew. Chem. Int. Ed. 2009, 48, 2759-2763.

\* cited by examiner (a) Unencapsulated control INS-1    (b) Encapsulated experimental INS-1

NANOBUBBLES

TECHNICAL FIELD

The present disclosure generally relates to a composition and a method of use, and in particular to a composition that can act as a carrier and break open by ultra sound to deliver its contents.

BACKGROUND

This section introduces aspects that may help facilitate a better understanding of the disclosure. Accordingly, these statements are to be read in this light and are not to be understood as admissions about what is or is not prior art.

Ultrasound is a valuable diagnostic imaging technique for studying various areas of the body, including, for example, the vasculature, such as tissue microvasculature. Ultrasound provides certain advantages over other diagnostic techniques. For example, diagnostic techniques involving nuclear medicine and X-rays generally involve exposure of the patient to ionizing electron radiation. Such radiation can cause damage to subcellular material, including deoxyribonucleic acid (DNA), ribonucleic acid (RNA) and proteins. Ultrasound does not involve such potentially damaging radiation. In addition, ultrasound is relatively inexpensive relative to other diagnostic techniques, including CT and MRI, which require elaborate and expensive equipment.

Ultrasound involves the exposure of a patient to sound waves. Generally, the sound waves dissipate due to absorption by body tissue, penetrate through the tissue or reflect off of the tissue. The reflection of sound waves off of tissue, generally referred to as backscatter or reflectivity, forms the basis for developing an ultrasound image. In this connection, sound waves reflect differentially from different body tissues. This differential reflection is due to various factors, including the constituents and the density of the particular tissue being observed. Ultrasound involves the detection of the differentially reflected waves, generally with a transducer that can detect sound waves having a frequency of one megahertz (MHZ) to ten MHZ. The detected waves can be integrated into an image which is quantitated and the quantitated waves converted into an image of the tissue being studied.

Ultrasound contrast agents are used to enhance the signal when imaging a patient using ultrasound. One interesting way to produce an ultrasound image is with a microbubble. Microbubbles are described as sphere or sphere-like ranging in size of greater than one micrometer, but smaller than one millimeter. Generally they are hollow with a gas core and vibrate when a sonic energy field is applied. The wave frequency emitted from the vibrating microbubble helps to produce an ultrasound image.

Another interesting use of a microbubble is to deliver a pharmaceutical agent to a tissue within the body. By encapsulating a pharmaceutical agent in a microbubble made up of a shell the pharmaceutical agent is delivered to a location prior to coming into contact with the cells and proteins which may alter its function, bioavailability, or concentration.

However, a drawback to the microbubbles and even nanobubbles currently known in the art is that they are too large and cumbersome for imaging or delivery of a therapeutic. What is needed is a smaller delivery mechanism that can travel into smaller vasculature and cross barriers between tissues and cells. More specifically it would be desirable to have a nanobubble that is small enough for imaging or delivery of a therapeutic. It would be further desirable if the nanobubble could be directed to the desired tissue and then have a therapeutic delivered at a specific time and place.

SUMMARY OF THE INVENTION

In one aspect of the present invention there is provided a nanobubble comprising a continuous outer shell, the outer shell comprising a cross-linked polymeric material, an inner wall of the continuous outer shell and a hollow core within the continuous outer shell. The nanobubble may be less than 250 nm in diameter. In a further aspect of the invention, the cross-linked polymeric material is a cellulose-based material.

In another aspect of the present invention, the outer shell may further comprise a fluorophore, a pharmaceutical, a biomolecule, a ligand, contrast imaging agents, antibodies, lipids, protein receptors, aptamers or combinations thereof. The hollow core may be filled with a solid, a liquid, a gas or combinations thereof.

DETAILED DESCRIPTION

Figure 1:
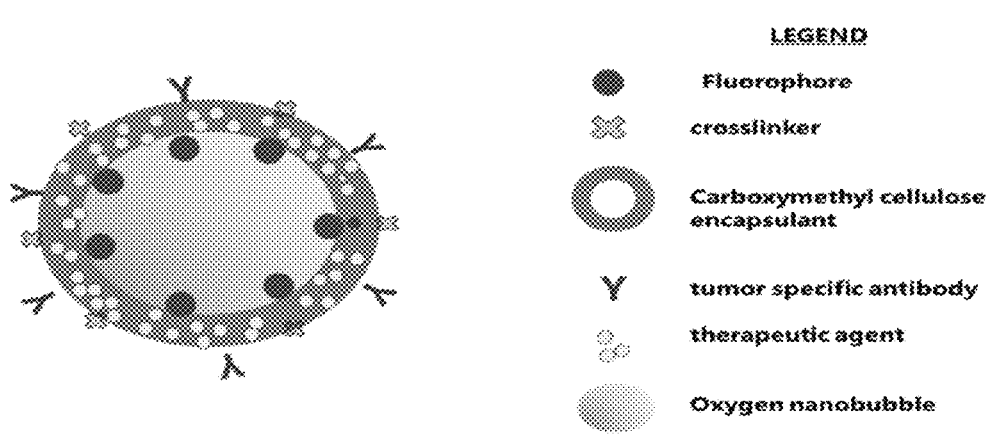
FIG. 1 is an illustrative graphic of one embodiment of a nanobubble incorporating at least one antibody and a therapeutic agent within the outer shell, and a fluorophore and oxygen encapsulated in the hollow inner core of the nanobubble.
Figure 2A:
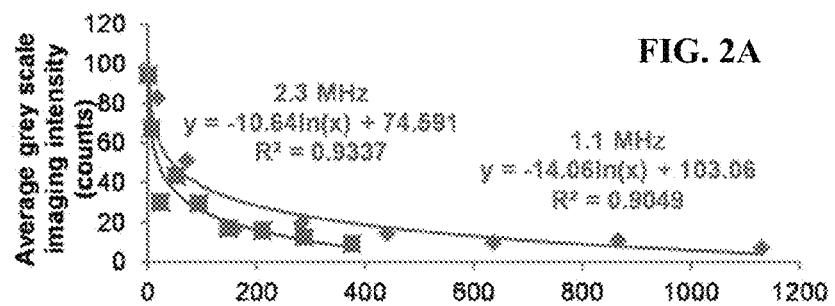
FIG. 2A is a graph showing ultrasound imaging intensity upon external ultrasound triggering of the nanobubbles at 1.1 MHz and 2.3 MHz, wherein the mean ultrasound imaging intensity decreases logarithmically and average oxygen release increases exponentially ($R^2$>0.80) at both frequencies.
Figure 2B:
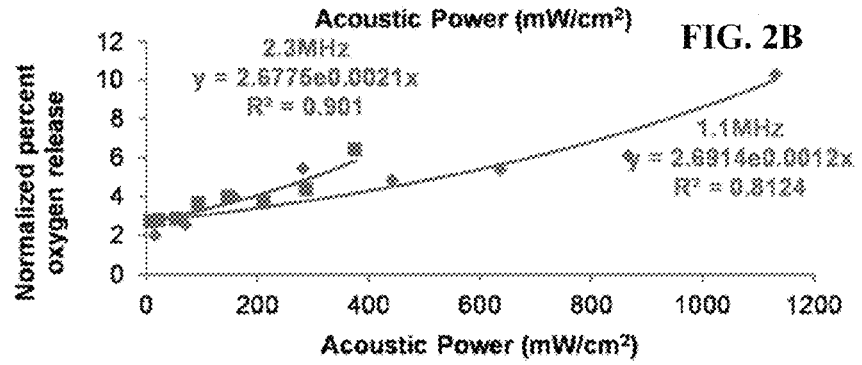
FIG. 2B is a graph showing oxygen release upon external ultrasound triggering of the nanobubbles at 1.1 MHz and 2.3 MHz, wherein the mean ultrasound imaging intensity decreases logarithmically and average oxygen release increases exponentially ($R^2$>0.80) at both frequencies.
Figure 3:
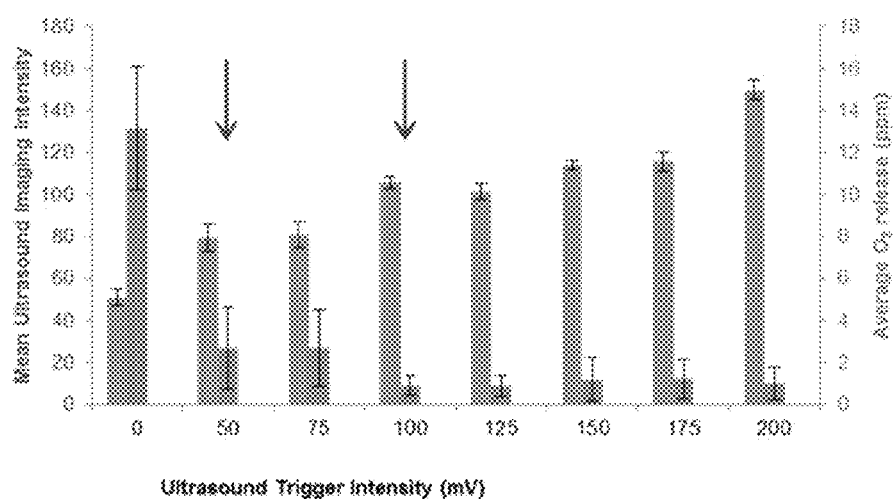
FIG. 3 is a graph showing ultrasound imaging intensity and oxygen release upon a longitudinal ultrasound trigger of the nanobubbles, where in the mean ultrasound imaging intensity decreases and average oxygen release increases significantly (* $p<0.001$) at external ultrasound trigger intensities of 50 and 100 millivolts (mV) (arrows)

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A novel composition is described. A nanobubble having a continuous outershell, an inner wall of the continuous outer shell, and a hollow core. In certain aspects the composition is a hollow, sphere or sphere-like shaped nanobubble ranging in size of about 10 nm diameter to about 250 nm diameter across. In certain aspects the hollow core of the nanobubble comprises biomolecules, liquids, small molecules, imaging agents, ultrasound contrast agents, or gases. In certain aspects the nanobubble is configured to image at least one cell, configured to deliver cargo to at least one cell, or configured to deliver a gas to at least one cell. In certain aspects the nanobubble is targeted to a specific cell or tissue. In certain aspects the nanobubble is configured to burst during a specific or range of frequencies provided by sound waves.

By "tissue" refers generally to specialized cells which may perform a particular function. It should be understood that the term "tissue," as used herein, may refer to an individual cell or a plurality or aggregate of cells, for example, membranes or organs. The term "tissue" also includes reference to an abnormal cell or a plurality of abnormal cells. Exemplary tissues include, for example, myocardial tissue (also referred to as heart tissue or myocardium), including myocardial cells and cardiomyocytes, membranous tissues, including endothelium and epithelium, laminae, connective tissue, including interstitial tissue, and tumors.

By "patient" refers to mammals, including humans, mouse, dog, cat, cow, pig, or horse.

By "internal region of a patient" and "region of interest" refer to the entire patient or to a particular area or portion of the patient. Internal regions of a patient and regions of interest may include, for example, areas being imaged with diagnostic imaging and/or areas being treated with a bioactive agent. Exemplary of such areas include, for example, the heart region, including myocardial tissue, as well as other bodily tissues, including the vasculature and circulatory system and cancerous tissue. The phrase "vasculature," as used herein, denotes the blood vessels in the body or in an organ or part of the body.

By "effective therapeutic amount" refers to an amount of a small molecule or biomolecule that is able to ameliorate, inhibit proliferation, reduce proliferation, or increase proliferation depending on the desired effect, type of molecule used, and concentration.

By "biomolecule" refers to substances which are capable of exerting a biological effect in vitro and/or in vivo. The bioactive agents may be neutral or positively or negatively charged. Examples of suitable bioactive agents include diagnostic agents, pharmaceuticals, drugs, synthetic organic molecules, proteins, peptides, vitamins, steroids and genetic material, including aptamers, nucleosides, nucleotides and polynucleotides.

By "biocompatible" refers to materials which are generally not injurious to biological functions and which will not result in any degree of unacceptable toxicity, including allergenic responses and disease states.

By "receptor" refers to a molecular structure within a cell or on the surface of the cell which is generally characterized by the selective binding of a specific substance. Exemplary receptors include, for example, cell-surface receptors for peptide hormones, neurotransmitters, antigens, complement fragments, and immunoglobulins and cytoplasmic receptors for steroid hormones. An exemplary receptor within the context of the present invention is the glycoprotein GPI-IbIIIa, which is a platelet integrin.

By "small molecule" or "pharmaceutical" or "drug" refers to any therapeutic or prophylactic agent which may be used in the treatment (including the prevention, diagnosis, alleviation, or cure) of a malady, affliction, disease or injury in a patient. Therapeutically useful peptides, polypeptides and polynucleotides may be included within the meaning of the term small molecule pharmaceutical or drug.

By "targeting agent" refers to refers to any material or substance which may promote targeting of tissues and/or receptors in vivo or in vitro with the compositions of the present invention. The targeting agent may be synthetic, semi-synthetic, or naturally-occurring. Materials or substances which may serve as targeting agents include, for example, proteins, including antibodies, glycoproteins and lectins, peptides, polypeptides, saccharides, including mono- and polysaccharides, vitamins, steroids, steroid analogs, hormones, cofactors, bioactive agents, and genetic material, including nucleosides, nucleotides and polynucleotides.

By "burst frequency" refers to the frequency or frequency range required to rupture the outer shell of the nanobubble to expose the cargo or inner contents within the hollow core to the outside environment, wherein the outside environment is in vivo or in vitro.

By "polymer" refers to molecules formed from the chemical union of two or more repeating units. Accordingly, included within the term "polymer" may be, for example, dimers, trimers and oligomers. The polymer may be synthetic, naturally-occurring or semisynthetic.

By "tumor" or "tumor cells" refers to an aggregate of abnormal cells and/or tissue which may be associated with diseased states that are characterized by uncontrolled cell proliferation. The disease states may involve a variety of cell types, including, for example, endothelial, epithelial and myocardial cells. Included among the disease states are neoplasms, cancer, leukemia and restenosis injuries.

By "power or intensity" refers to the sound power and sound intensity, which are well defined in the field of physics. Briefly sound power is the amount of energy produced over a given period of time from a mechanical motion such as vibration. Sound intensity is related to sound power in that it describes the sound power over a given physical area.

The composition of a nanobubble may comprise an outer shell of a polymer material. This polymer material is chosen from the group consisting of sodium carboxymethyl cellulose (NaCMC), cellulosic materials, polyethylene glycol (PEG), chitosan, sodium hyaluronate, poly(lactic-co-glycolic acid, polystyrene, hydrogels, superdisintegrants, pharmaceutical excipients, sodium starch glycolate, poly (vinyl pyrrolidone), microcrystalline cellulose, hydroxypropylmethyl cellulose, HPMC phthalate, oxycellulose, sodium stearyl fumarate, alpha cellulose, pre gelatinized starch, starch acetate, albumin, dextran, or chitosan. The outer shell of a polymer material is cross-linked. General ways to crosslink include chemical means, photo-reactive means, thermal means, pH means, electron beam exposure, gamma radiation, UV radiation, oxidative crosslinking, or photochemical all of which are known to those of ordinary skill in the art. The continuous outershell of the nanobubble may include pores generated by the polymer material, the crosslinks, or both.

The outer shell of the nanobubble may also comprise fluorophores, small molecules such as pharmaceuticals, biomolecules such as growth factors, glucose, steroids, ligands for targeting such as prostate-specific membrane antigen PSMA or folate, sticky molecules, ultrasound contrast imaging agents, antibodies in whole or in part, lipids, protein receptors, or aptamers such as an oligonucleic acids or peptide molecules. These additional elements may be added as single additions or in combinations on a single nanobubble. For example, a nanobubble may comprise an outer shell material including a targeting ligand and a small molecule. The nanobubble may comprise an outer shell material and an antibody. The purpose of these additional elements are for various applications including imaging, targeting, treating, or causing a molecular response to at least one cell or tissue.

The hollow core of the nanobubble will have about the same diameter as the nanobubble itself. The hollow core may comprise cargo of a solid, liquid or gas for various applications. Additional elements described previously, fluorophores, small molecules such as pharmaceuticals, biomolecules such as growth factors, glucose, steroids, ligands for targeting such as prostate-specific membrane antigen PSMA or folate, sticky molecules, antibodies in whole or in part, ultrasound contrast imaging agents, lipids, protein receptors, or aptamers such as an oligonucleic acids or peptide molecules, may be bound to the inner wall of the outer shell and directed towards the hollow core of the nanobubble. The additional elements in the hollow core may be free-floating, or unattached to the inner wall of the outer shell of the nanobubble. The hollow core may comprise a gas including but not limited to oxygen, nitrogen, carbon dioxide, plasma, perfluorocarbons, perfluorohexane, or tetradecafluorohexane. The hollow core of the nanobubble may comprise a liquid including but not limited to water, contrast imaging agents, saline solution, perfluorocarbon, fluorinated liquids, liquid drug formulations, nitric oxide, chemical oxygen generators, or oxygen release compounds.

The nanobubble may be configured carry a cargo of solid, liquid, or gas. A means for carrying cargo is described and illustrated in example 1 and 2 of this application. The nanobubble may be configured to carry a combination of cargo including ratios of at least two solid:solid, solid:liquid, solid:gas, liquid:liquid, liquid:gas, gas:gas, or solid:liquid:gas. The nanobubble's cargo is only limited by the amount of cargo that can fit into the available space in the hollow core of the nanobubble.

The nanobubble may be configured to burst under certain conditions. In one aspect the nanobubble is configured to burst at a given frequency or power or intensity of sound wave or any external form of energy source such that the nanobubbles resonate and burst. The frequency or power or intensity at which the nanobubble bursts may be tuned and is controlled in part by the polymer material and number and type of cross links. For example, by increasing the number of cross-links comprising the outershell of the nanobubble may increase the burst frequency required to burst the nanobubble. In another aspect the size of the nanobubbles can be tuned to initiate bursting at different frequencies or power or intensity. Thus multi-modal drug release is possible where timely and sequential release can be programmed and a plurality of nanobubbles tuned to release a plurality of drugs only upon excitation by that frequency or power or intensity. One of skill in the art will recognize that different applications will require different burst frequencies or power or intensity. As a non-limiting example, the nanobubble may be configured to burst at 1.1 MHz over a range of about 0.01 to about 1,100 mv/cm$^3$, wherein 50 percent (%) of the nanobubbles configured to burst in this range will burst at about 70 mv/cm$^3$. In another non-limiting example, the nanobubble may be configured to burst at 2.2 MHz over a range of about 0.01 to about 400 mv/cm$^3$, wherein 50% of the nanobubbles configured to burst at this frequency will burst at about 30 mv/cm$^3$. A plurality of nanobubbles may be generated to burst at different frequencies depending on the application. This heterogenous mix of nanobubbles may be delivered to a mammal or patient at or about the same time or at different times.

The nanobubbles may be delivered in vitro or in vivo. Methods of delivering the nanobubbles will be understood to those of skill in the art. Methods of delivery include but are not limited to, injection, inhalation, intravascular, intradermal, catheter, injection into a port, oral delivery, or transmucosal. The nanobubbles may delivered with an acceptable pharmaceutical carrier including but not limited to saline, of which is well known in the art.

In certain applications, the nanobubbles may be configured to deliver oxygen to at least one cell, group of cells, or tissue. The amount of oxygen carried in a nanobubble is dependent on the nanobubble's size but may range in concentration from about 20,000 to 200,000 ppm. If the nanobubble comprises pores, some of the oxygen will diffuse out from the inner core and through the continuous outer shell. These nanobubbles configured to carry oxygen may be delivered by any of the previously described mechanisms.

Nanobubbles comprised to carry oxygen may be used as contrast imaging agents or as a therapeutic. See below examples 1 through 3. If the nanobubble is used to deliver oxygen as a contrast agent, it may be provided in combination with other known contrast imaging agents. The combination may be delivered in a single nanobubble, in separate nanobubbles, or an oxygen comprising nanobubble and a contrast imaging agent not associated with a nanobubble. The oxygen comprising nanobubble may also include targeting agents to direct the nanobubble to a specific cell or tissue type of interest. Targeting agents are well known to those of skill in the art and include but are not limited to EGF, VEGF, PSMA, antibodies in whole or in part, or folate.

Nanobubbles configured to carry oxygen and be used as a therapeutic may be delivered in combination with other therapeutics. The combination of therapeutics may be delivered in a single nanobubble, separate nanobubbles, or an oxygen comprising nanobubble and a therapeutic not associated with a nanobubble. The nanobubble configured to carry oxygen in combination or not with a therapeutic will be configured to burst at a specific frequency to burst the nanobubble and fully deliver its cargo contents to the surrounding cells or tissue. The oxygen comprising nanobubble for use as a therapeutic may be targeted using a targeting molecule. Targeting agents are well known to those of skill in the art and include but are not limited to EGF, VEGF, PSMA, antibodies in whole or in part, or folate. In certain aspects the nanobubble comprising oxygen as a therapeutic will not have a targeting agent and instead will be delivered to a diseased cell, such as cancer, through "leaky vasculature" through a phenomenon known as enhanced permeability and retention (EPR). This phenomenon is well known in the art and is taken advantage of by many in the cancer therapeutic space.

Example 1 Method of producing nanobubbles. Our approach was to cross link a sodium carboxymethyl cellulose (NaCMC) hydrogel (FMC Biopolymer) while encapsulating the oxygen nanobubbles inside the gel using a layer-by-layer (LBL) approach. Carboxymethyl cellulose is a FDA-approved pharmaceutical excipient that is non-cytotoxic and inexpensive, and possesses large drug-loading capacity and robust chemistry. Briefly, sodium carboxymethyl cellulose (Ac-Di-Sol, FMC Biopolymer, Philadelphia, Pa.) was dissolved in nanopure water to form a 0.1% (w/v) gel and homogenized and saturated with oxygen gas (UHP grade). The oxygen inlet was connected with an air nozzle (Nano Super Air Nozzle 1110SS, EXAIR Corporation) and a 20 nm membrane filter (Emflon II, Pall Corporation) to help generate oxygen nanobubbles. Further, the carboxymethyl cellulose solution was sonicated simultaneously with a probe horn (Cell Disruptor, Ultrasonic Power Corporation) and a bath sonicator (Model 2210, Branson Ultrasonics) since ultrasonic energy helps sonic compression of oxygen microbubbles to produce oxygen nanobubbles in the solution. 1% aluminium chloride ($AlCl_3$) cross linking agent was added to form the encapsulation structure under continuous ultrasonication. Aluminium chloride is a trivalent crosslinker and helps decrease the drug release rate compared to bivalent crosslinkers. Aluminium chloride also serves as a strong electrolyte and increases the electrostatic repulsive force to balance out the size reduction forces of the nanobubble, thus stabilizing the nanobubble. The pH of the resulting nanobubble suspension was neutralized to pH 7 using 0.1% ammonium hydroxide ($NH_4OH$) solution added dropwise.

Figure 4:
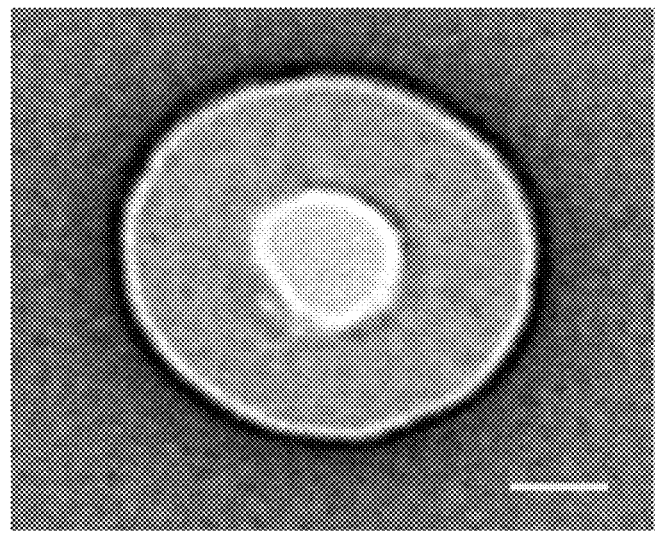
FIG. 4 is a transmission electron microscopy image of a nanobubble with an oxygen compartment in the inner core and surrounded by a cellulosic outer shell, wherein the scale bar equals 50 nanometers (nm)
Figure 5:
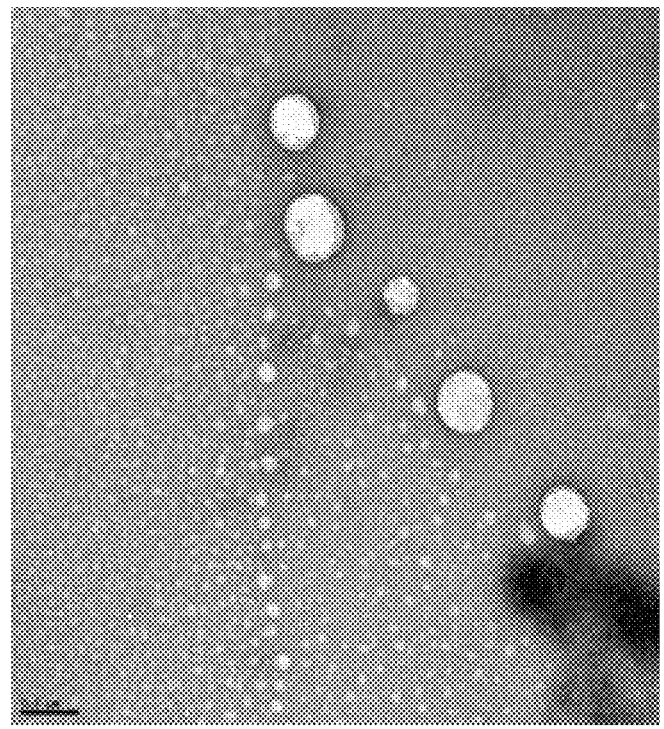
FIG. 5 is a transmission electron microscopy of nanobubbles showing size distribution of 20-200 nm, wherein the scale bar equals 100 nanometers (nm)
Figure 6:
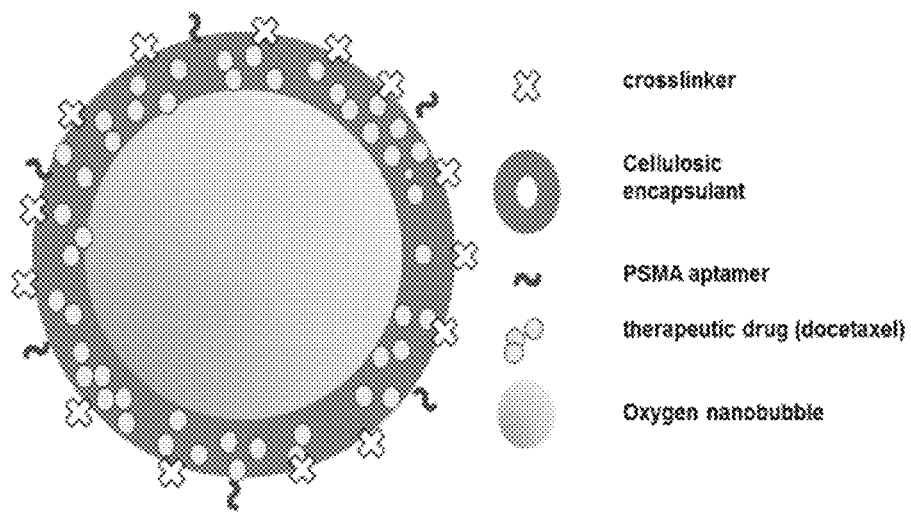
FIG. 6 is a graphic representation of one embodiment of a nanobubble incorporating a therapeutic drug and a targeting agent in a crosslinked, cellulosic outer shell, and a hollow inner core comprising oxygen.
Figure 7:
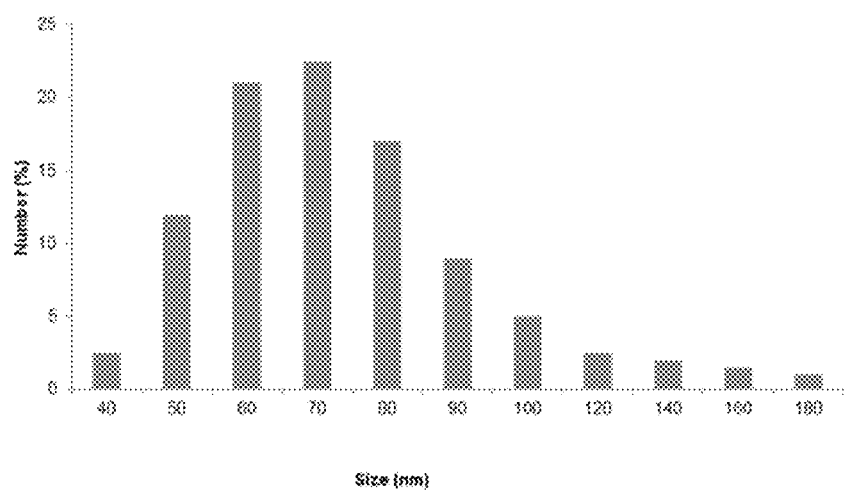
FIG. 7 is a graph showing the range of diameters or sizes of the nanobubbles produced during several experiments, with the most common size ranging between 60 and 80 nm.
Figure 8:
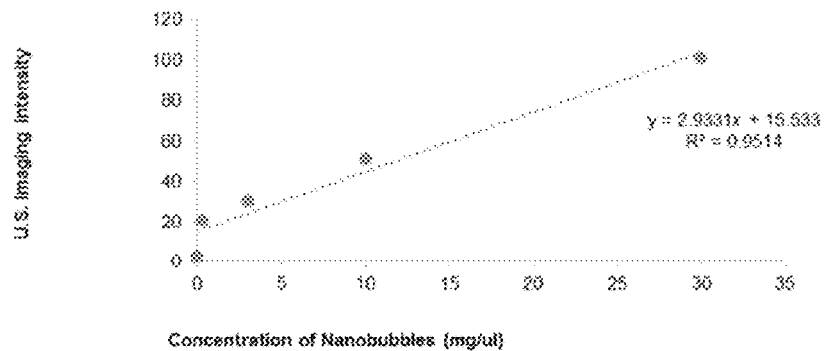
FIG. 8 is a graph illustrating the mean ultrasound (U.S.) imaging intensity increases upon increase in nanobubble concentration.

To synthesize the second batch of nanobubbles with drug and fluorophore, docetaxel (0.5 mg/ul in DMSO) and Alexa Fluor 647 (5 ug/mL) is injected into the NaCMC solution prior to crosslinking Encapsulation of drug inside a contrast-enhancing nanobubble contrary to co-injection of the two is expected to reduce side-effects since it will prevent extravasation of the drug. The surface of the polymer is covalently conjugated with PSMA aptamers (PSMA A10, Integrated DNA Technologies Inc.) for targeting prostate specific membrane antigens (PSMA) which are overexpressed in over 80% of prostate carcinomas. Acidic pH of the nanobubbles before neutralization is expected to assist in conjugation of the aptamers to the nanobubbles. Our preliminary results indicate that aptamer conjugation was successful with ~70% conjugation efficiency determined using a Nanodrop spectrophotometer. The size of the nanobubbles in this example was less than 200 nm as evaluated using transmission electron microscopy (TEM) (FIG. 4 and FIG. 5) and dynamic light scanning (DLS) (FIG. 7). Washing steps were incorporated to ensure pH neutralization and the nanobubble was freeze dried and re-suspended in PBS to achieve the desired concentration.

To optimize the size of the nanobubble to achieve optimum ultrasound contrast intensity, a sequential factorial experiment design and response surface methodology is performed using temperature (0° C. to 37° C.), pH of solution (5 to 9), ultrasound intensity (40 MHz and 70 MHz), and concentration of crosslinker (0.1% to 1%) and NaCMC (0.1% to 2%) as parameters. The synthesis steps to produce oxygen nanobubbles with a range of sizes between about 10 nm and 250 nm that can be excited at specific intensities for imaging and burst release. The nanobubbles act as a contrast agent under low-intensity (40-70 MHz) ultrasound and burst collapse when subjected to resonant high intensity (1.1 MHz focused frequency) ultrasound. Thus, the nanobubbles can first locate a tumor by ultrasound imaging at a low-intensity and then can be selectively burst to release the drug at the tumor site via sonoporation.

Figure 19:
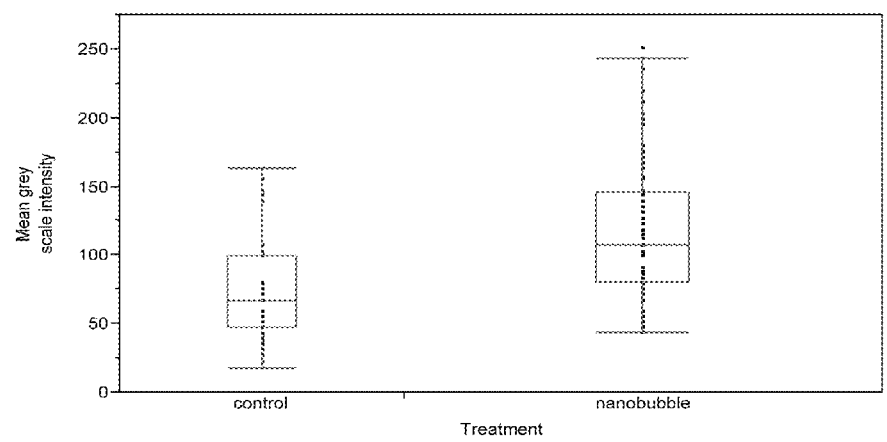
FIG. 19 is a graph depicting a graphical comparison of the mean grey scale intensities of control and nanobubble introduced samples, wherein the significant increase in the mean signal intensity is credited to the contrast generated by the nanobubbles.
Figure 20:
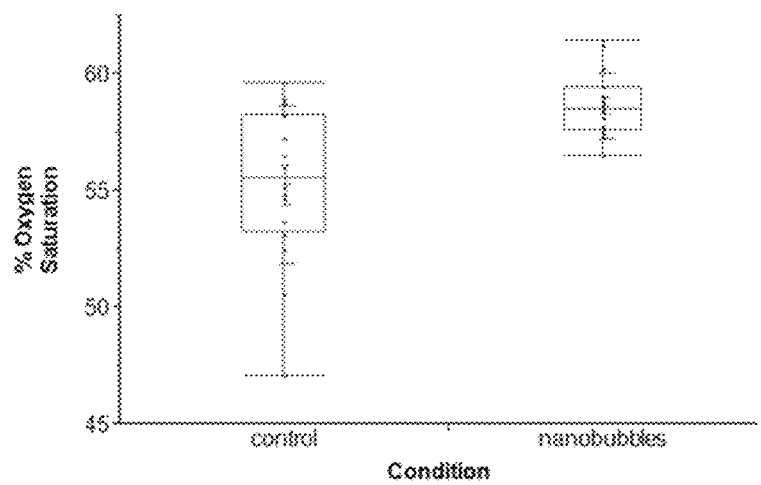
FIG. 20 is a graph depicting the increase in the oxygen levels in the cell culture media in case of the nanobubble treated sample is significant when compared against the control sample.
Figure 21:
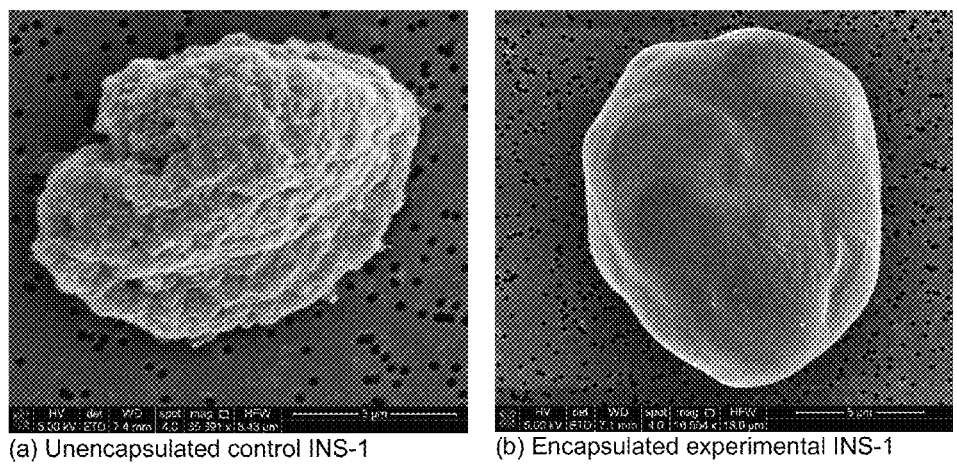
FIG. 21 is two electron microscopy images of an islet cell (INS-1) where on the left the cell is unencapsulated and the cell on the right is encapsulated by an outer shell consisting of carboxymethyl cellulose and oxygen but not limited to these materials.
Figure 22:
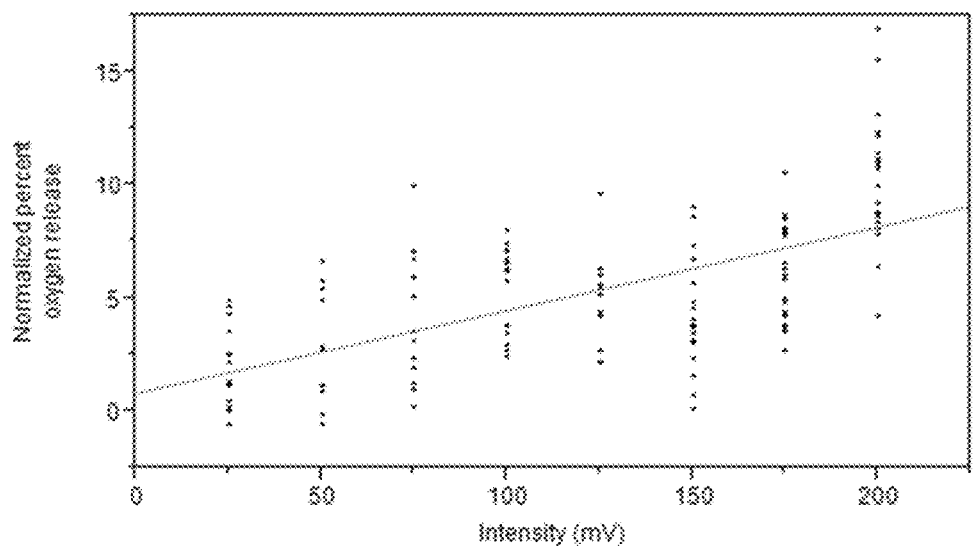
FIG. 22 is a graph depicting normalized percent oxygen release linearly increases upon increase in external ultrasound intensity ($p<0.0001$), wherein the external ultrasound frequency is set at 1.1 MHz.
Figure 23:
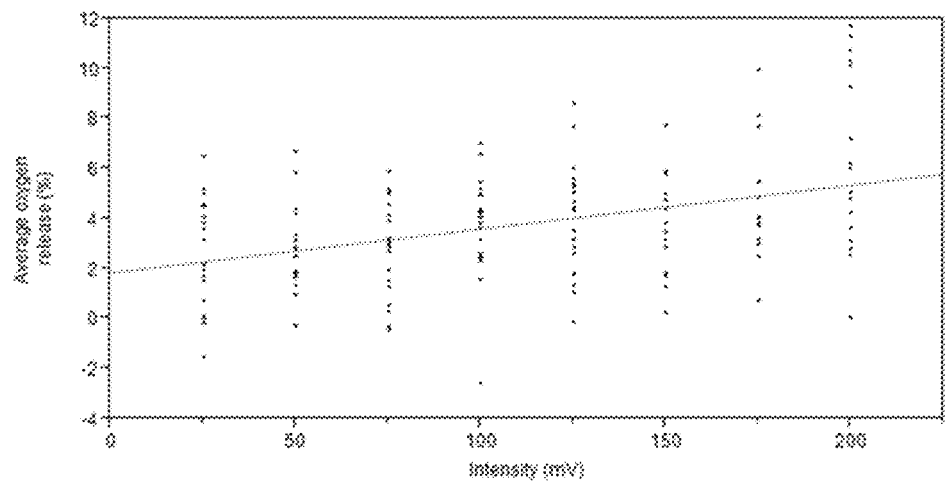
FIG. 23 is a graph depicting normalized percent oxygen release linearly increases upon increase in external ultrasound intensity ($p<0.0001$), wherein the external ultrasound frequency is set at 2.2 MHz.
Figure 24:
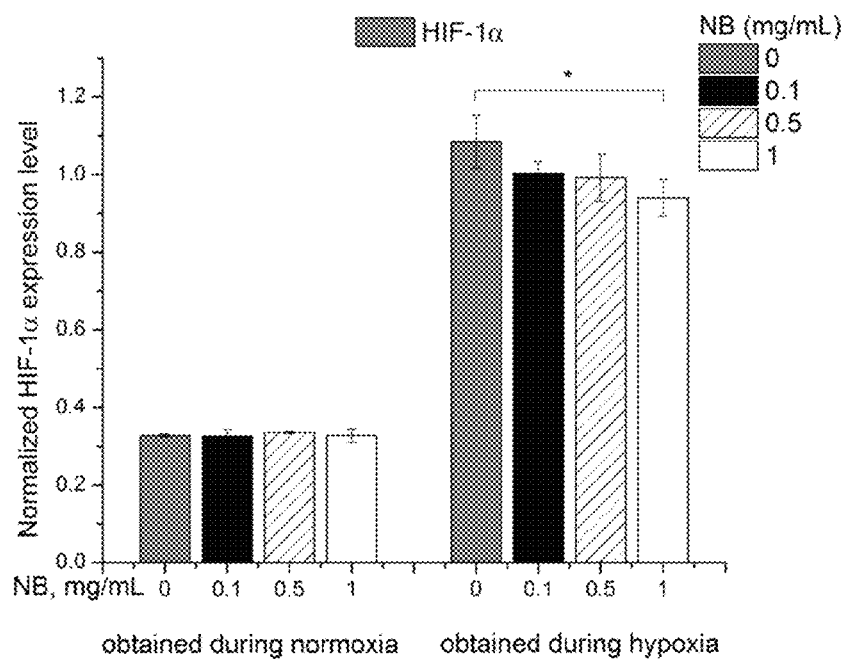
FIG. 24 is a graph denoting HIF-1A protein expression levels obtained for different treatment conditions and nanobubble (NB) concentrations (mg/mL)
Figure 25:
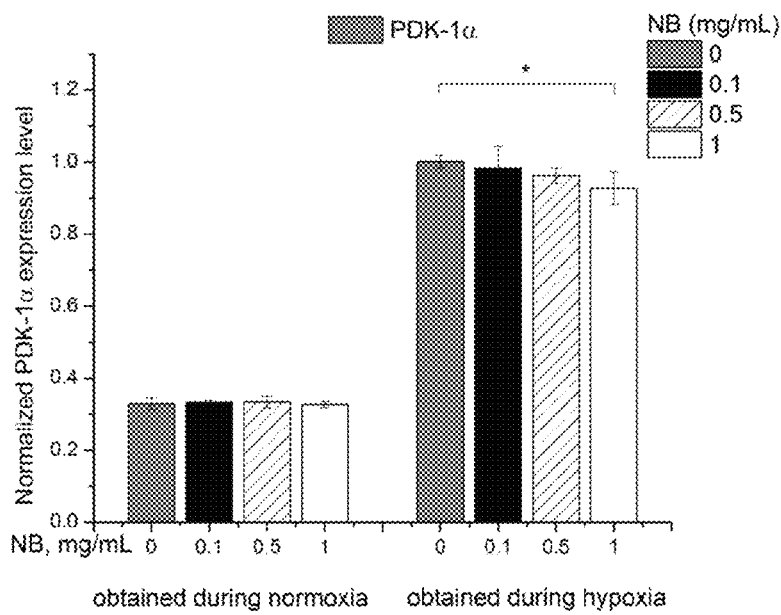
FIG. 25 is a graph denoting PDK1 protein expression levels obtained for different treatment conditions and nanobubble (NB) concentrations (mg/mL).

Example 2 of Oxygen Nanobubbles as imaging an agent. Ultrasound image of the signal generated from subcutaneous injection of equal volume of nanobubbles and saline. FIG. 19 is a graph displaying averaged mean grey scale intensity within the region of interest corresponding to the injected solutions. Note that there is significant difference between the two images suggesting a strong ultrasound contrast generated in vivo using the nanobubbles.

Figure 9:
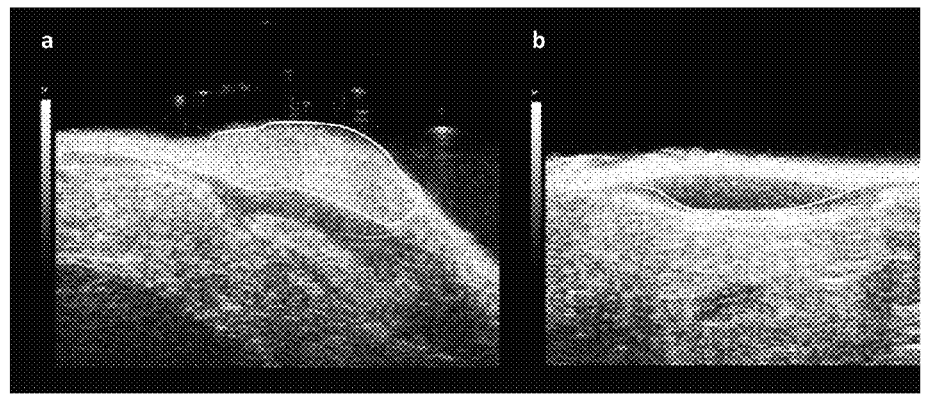
FIG. 9 shows two images the first on the left (a) shows unburst oxygen bubbles after they were injected subcutaneously under the dermis of a mouse, and the second picture on the right (b) shows a dark spot where saline was injected subcutaneously under the dermis of a mouse.
Figure 10:
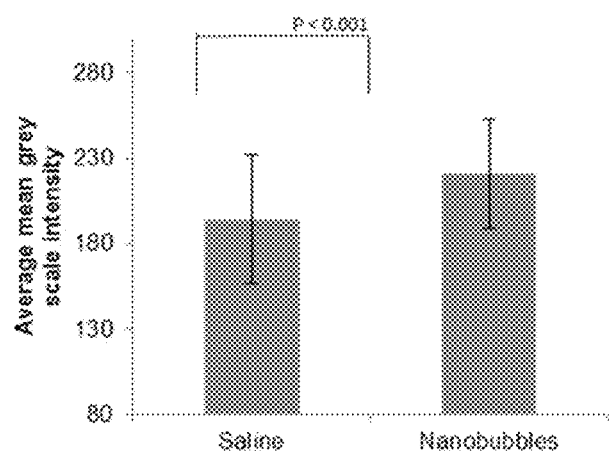
FIG. 10 is a graph showing the averaged mean grey scale intensity within the region of interest corresponding to the injected solutions (i.e. nanobubbles or saline), and note that there is significant difference between the two images suggesting a strong ultrasound contrast generated in vivo using the nanobubbles.
Figure 11:
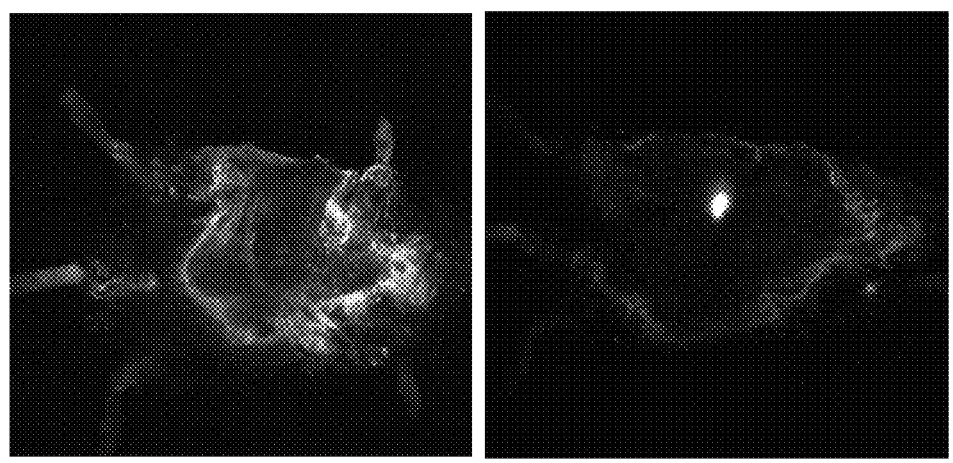
FIG. 11 shows two images with the one on the right showing the autofluorescence of a mouse's whole body after being injected with saline, and the image on the left showing the autofluorescence of a mouse's whole body upon being injected subcutaneously with nanobubbles, thus illustrating significant fluorescence intensity enhancement and nanobubble localization.
Figure 12:
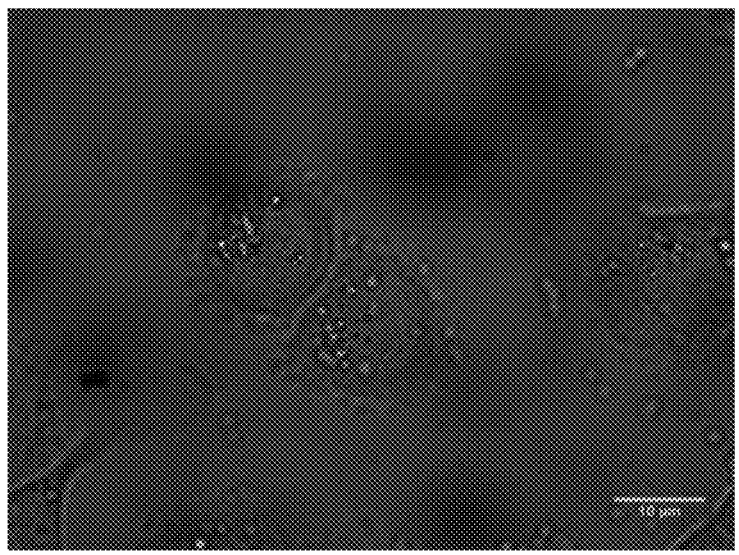
FIG. 12 is a bright field microscope image of HeLa cells that have taken up nanobubbles comprising oxygen and a fluorescence molecule FitC.
Figure 13:
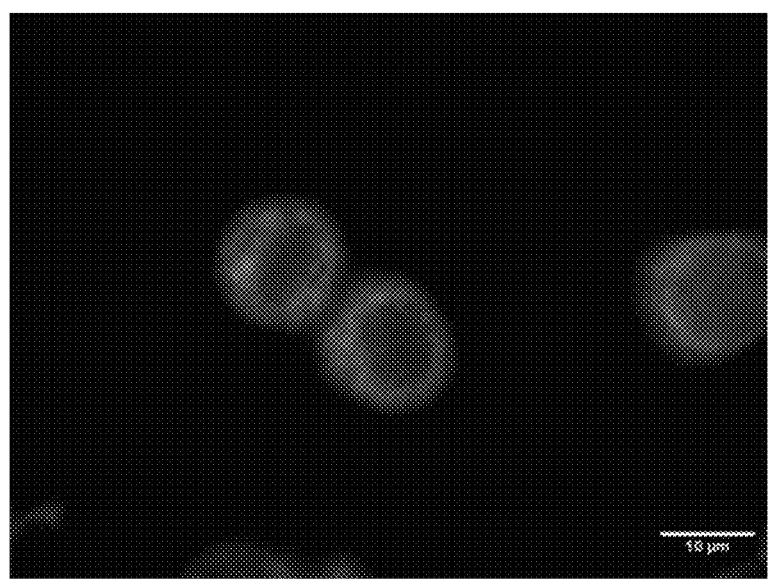
FIG. 13 is an epifluorescence microscope image (488 nm emission rays) of HeLa cells which have taken up nanobubbles comprising oxygen and FitC, and the location of the fluorescent molecules signifies the localized position of the nanobubbles.
Figure 14:
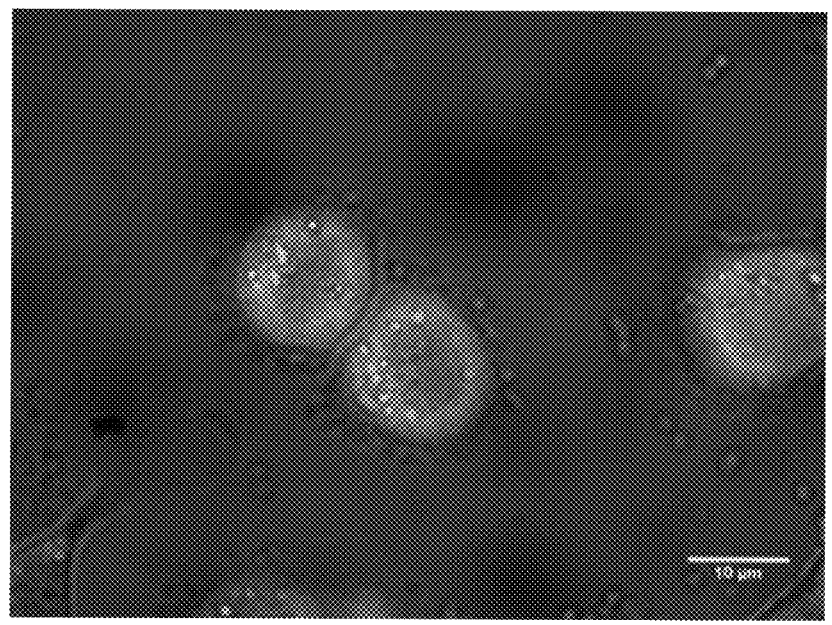
FIG. 14 is a superimposition of the bright field and the fluorescent images, wherein the fluorescent signal is strongest over the position of the cells, and thus it is concluded that the nanobubbles have been taken up by the cells thereby concentrating inside the cells.
Figure 15:
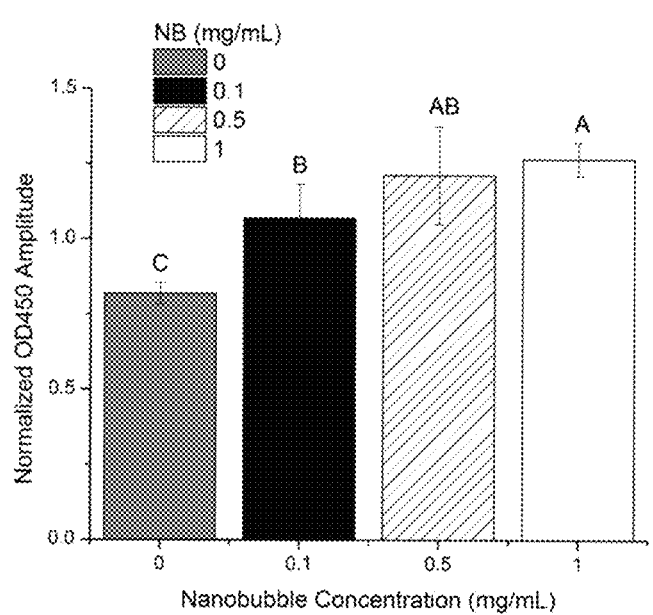
FIG. 15 is a graph showing 5 mC methylation levels as measured against varying concentration of nanobubble treatments.
Figure 16:
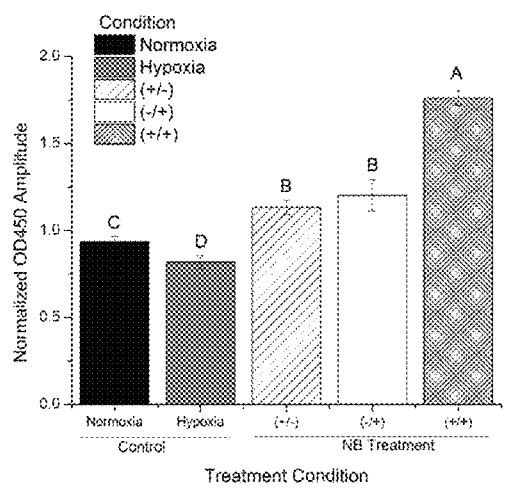
FIG. 16 is a graph showing 5 mC methylation levels as measured for the varying treatments, and 0.5 mg/mL nanobubble concentration, to identify the relation between treatment frequency and the total time of incubation.
Figure 17:
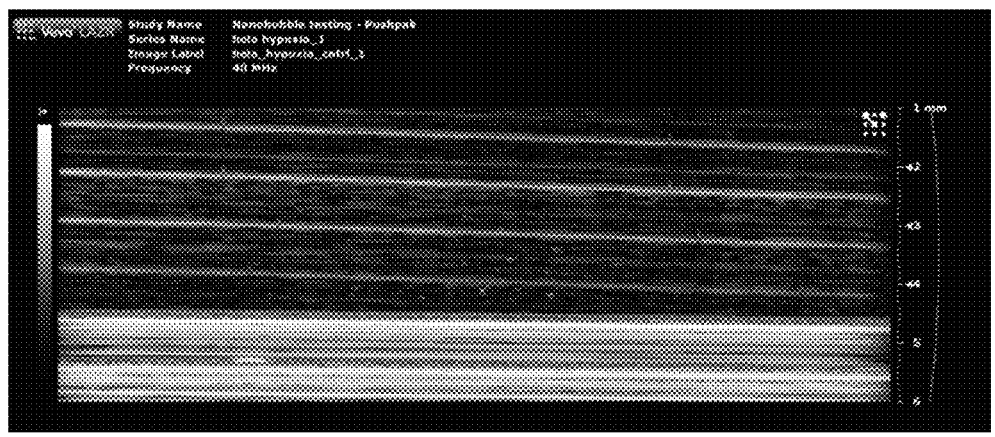
FIG. 17 is an image showing control ultrasound image on agarose base and D.I water. No nanobubbles were added for this image.
Figure 18:
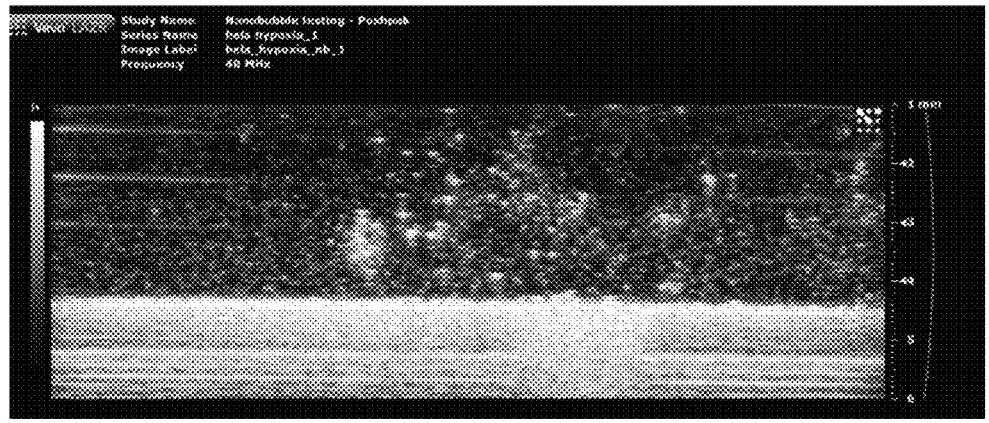
FIG. 18 is an image showing ultrasound image to visualize nanobubbles, wherein the contrast generated is because of the oxygen nanobubbles.

The approach is to inject the nanobubbles and saline control subcutaneously to nude male BALB/c mice without tumors and observe the ultrasound intensity, velocity, speed and direction of movement, strain rate, volume, and perfusion of the injected nanobubble. Mice are anesthetized and observed using Vevo 2100 ultrasound platform and Kodak whole animal fluorescence imaging system. Results show that nanobubbles have significantly greater ultrasound contrast compared to saline as illustrated in FIG. 9. Further, by using intravenous injections of the nanobubble one can evaluate the circulation and perfusion characteristics of the nanobubble.

The ultrasound trigger platform to burst the nanobubbles is generated by aligning the ultrasound trigger transducer to the subcutaneous injection site. Ultrasound imaging intensity is compared for different transducer frequencies and amplitudes employed and optimal settings are calculated. Finally, oxygen measurements are carried out using an optical sensor (NeoFox, Ocean Optics Inc., FL) and the data is correlated with the ultrasound contrast intensity. After completion of the time frame of observation, the mouse organs are harvested and histopathologically analyzed. Histopathological analysis provides a measure for quantifying nanobubble uptake and also shows cytotoxicity, if any.

Example 3 of oxygen nanobubbles incorporating oxygen and using oxygen as a treatment. Briefly, sodium carboxymethyl cellulose (Ac-Di-Sol, FMC Biopolymer, Philadelphia, Pa.) was dissolved in nanopure water to form a 0.1% (w/v) gel and homogenized and saturated with oxygen gas (UHP grade). The oxygen inlet was connected with an air nozzle (Nano Super Air Nozzle 1110SS, EXAIR Corporation) and a 20 nm membrane filter (Emflon II, Pall Corporation) to help generate oxygen nanobubbles. Further, the carboxymethyl cellulose solution was sonicated simultaneously with a probe horn (Ultrasonic Power Corporation Cell Disrupter) and a bath sonicator (Branson 2210) since ultrasonic energy helps sonic compression of oxygen microbubbles to produce oxygen nanobubbles in the solution. Fluorescin isothiocynate isomer I fluorophore (5 ug/mL) was injected into the sonicated NaCMC gel to enable fluorescence imaging. Finally, 1% aluminium chloride ($AlCl_3$) cross linking agent was added to form the encapsulation structure under continuous ultrasonication. Aluminium chloride is a trivalent crosslinker and helps decrease the drug release rate compared to bivalent crosslinkers. Aluminium chloride also serves as a strong electrolyte and increases the electrostatic repulsive force to balance out the size reduction forces of the nanobubble, thus stabilizing the nanobubble. The pH of the resulting nanobubble suspension was subsequently neutralized to pH 7 using 0.1% ammonium hydroxide ($NH_4OH$) solution added dropwise.

A new culture of HeLa cells was treated with 1.0 mg/mL of oxygenated nano-bubble (conjugated with Fluorescein isothiocyanate-FitC) solution. After incubation of 24 hours the cells were viewed and imaged under a confocal microscope. Epifluorescence images were obtained with an emission of 488 nm. Olympus IX71® Inverted Microscope with a 20× objective lens (Olympus UIS2) was used to view the cell sample. Images were captured through QCapture software.

Ultrasound imaging was carried out using Vevo 2100 ultrasound imaging system (FujiFilm isualSonics Inc., Toronto CA) equipped with a 22-55 MHz microscan transducer (MS550D, Vevo 2100) operated at 40 MHz. Imaging focal planes, brightness, and contrast were kept constant for all the experiments. Transducer tip was immersed 0.5 cm into the water. To observe the concentration dependence of ultrasound imaging intensity, different concentrations of nanobubbles (Table 1) were injected into 10 mL DI water placed on top of 5 cm 1% agarose gel phantoms. Images were processed using ImageJ (Research Services, National Institute of Health) software. To obtain in vitro ultrasound images, HeLa cells were incubated on 8 $cm^2$ (CLS3294-Sigma Aldrich) culture plates with 10 mL culture media for 24 h with and without nanobubbles. Further, the culture plates were imaged using the same ultrasound imaging setup with the transducer tip immersed 0.5 mm into the media from above the plate. A region of interest was loaded onto each image and mean grey scale intensity was quantified. The data was exported to JMP software for statistical analysis.

In vitro oxygen measurements were conducted using the NeoFox Phase Measurement system (Ocean Optics). Oxygen flux was measured through the Fiber Optic Oxygen Sensor Probe "-R" (Ocean Optics); and the NeoFox Viewer Software was employed to record the oxygen measurements. The fluorescence based oxygen measurements were conducted in the culture flasks itself. The probe was calibrated using the two-point method with 0% Oxygen (Argon) and 20% Oxygen (Air) as the calibration points. In order to take the measurements, the probe was dipped into the cell culture media present in the experimental culture flasks. Oxygen measurements were recorded for two culture step ups: negative control; and culture treated with 500 uL of 0.5 mg/mL oxygenated nanobubble solution. Both the cell cultures were incubated under hypoxic conditions (hypoxic incubator) for 24 hours.

The nanobubble may be configured to carry therapeutics to a diseased location within a patient. The amount of therapeutic delivered will be an effective amount, which is known to those of skill in the art. The nanobubble configured to carry a therapeutic may be used to treat, inhibit, or reduce the symptoms of solid tumors, blood tumors, circulating tumor cells, bacterial infection, viral infection, inflammation, oxygen-starved environment, autoimmune disorders, diseases of the brain, spine, kidneys, stomach, lungs, eye including glaucoma, optic nerve, gastro-tract, intestines, colon, bladder, ovaries, prostate, lymphatic system, circulatory system, bone, muscle, liver, pancreas, heart, trachea, or inner ear. The therapeutic may be a small molecule, pharmaceutical agent, biomolecule, radiotherapeutic, large molecule, inhibitor, protease, antibiotic, antiviral, a combination product including a biomolecule and synthetic molecule, or siRNA, aptamers, DNA, antibodies, RNA depending on the disease being treated, inhibited, or symptoms reduced. The delivery mechanism of the therapeutic includes but is not limited to injection, inhalation, intravascular, intradermal, catheter, injection into a port, oral delivery, or transmucosal. The nanobubble configured to carry a therapeutic may comprise a continuous polymer outer shell including a targeting agent to direct the nanobubble and its cargo to a specific cell or tissue type. In other embodiments the nanobubble configured to carry a therapeutic comprises a continuous polymer outer shell and no targeting agent.

The nanobubble configured to carry a therapeutic is configured to burst at a specific frequency. The nanobbuble may be delivered with a plurality of other nanobubbles which are configured to burst at around the same burst frequency or at different burst frequencies. A combination of burst frequencies is useful if delivering a combination therapy. For example a specific application may require at least two different drugs to be provided to a tissue for the desired effect. The first drug is carried by a first nanobubble configured to burst at a first burst frequency and a second drug is carried by a second nanobubble configured to burst at a second burst frequency. The first burst frequency does not overlap significantly with the second burst frequency which allows for selectively triggering the release of the first drug over the second drug localized near the tissue.

Example 4 illustrating therapeutic delivery to an animal model. This example observes the nanobubble characteristics in mice xenografted with LNCaP tumors at multiple timepoints. Briefly, 8-10 week old male nude BALB/c mice (Jackson Labs, stock #002019) were xenografted with LNCaP cells in Matrigel (1:1 volume ratio). The tumor is imaged using the Vevo 2100 ultrasound imaging system every day after xenografting and serves as control for our experiments. 2D and 3D volumetric quantification of the tumors and monitoring of tumor development is repeatedly and longitudinally monitored in the same mouse using the ultrasound machine. One week after tumor inoculation, the nanobubble dose (mg/mg) is injected via the lateral tail vein with the mice under anesthesia. Further, the mice are divided randomly into two groups to evaluate the effect of the external ultrasound pulse trigger in bursting the nanobubbles. Ultrasound bursting pulse (0.1-2 mW/cm$^2$) using the single element transducer at the optimal frequency determined by the in vivo optimization results provides bursting of the nanobubbles and drug release. Tumor size is monitored and it is expected that tumor size will significantly reduce in the mice treated with the external bursting pulse. Burst release of the drug provided a first order drug release and efficient uptake of the nanobubble by the cells because of sonoporation. On the contrary, the mice group without external ultrasound trigger is expected to have a lower decrease in tumor size. Images are analyzed for mean grey scale intensity using ImageJ software. All imaging and analysis is carried out using the same focal planes, focal depth, and region of interest. Oxygen measurements in vivo are performed using optical fluorescence oxygen sensor (NeoFox) and the data is correlated with the ultrasound trigger frequency. Oxygen release data obtained is expected to provide confirmation for effectiveness of targeting of the nanobubble. Pharmacokinetic (PK) and pharmacodynamics (PD) of the drug is evaluated using HPLC/MS. Finally, the mice are euthanized and their organs are harvested for histopathological and fluorescence analysis.

The nanobubble may be configured to act as an imaging agent in vivo. The nanobubble may comprise a continuous outer shell, inner wall of the outer shell, and hollow inner core. The inner core of the nanobubble comprises a contrast agent which may be a liquid or a dye. These liquids are known in the art and some become gaseous at body temperature. Other examples include fluorinated compounds such as perfluorocarbon, perfluorohexane, tetradecafluorohexane, or Fluorinert FC-72. The nanobubble may include a targeting agent to direct the nanobubble to a specific cell or tissue type.

The amount of contrast agent included in a nanobubble is dependent upon its size but may range in concentration between about 0 to about $5 \times 10^{-15}$ cm$^3$ concentration. The delivery mechanism of these nanobubbles configured to carry a contrast imaging agent include but are not limited to injection, inhalation, intravascular, intradermal, catheter, injection into a port, oral delivery, or transmucosal.

These nanobubbles configured to carry a contrast agent are configured to specifically not burst below the burst threshold. The burst threshold is set to a frequency higher than is needed to generate an image using an imaging device, specifically ultrasound. This threshold number will change depending on the application and location of the nanobubble comprising contrast agent. Applications of nanobubbles as an imaging agent include imaging a solid tumor, circulating tumor cells, liquid tumors, metastatic tumors, organs including heart, lungs, pancrease, prostate, kidneys, stomach, imaging pancreatic islets, imaging for the identification of a specific protein in a tissue or cell, imaging cholesterol in a tissue or cell, imaging lipids in a tissue or cell, or imaging the uptake of the nanobubble into a specific cell or tissue type for example by endocytosis.

Contrast imaging agent nanobubbles may be used to diagnose or detect where a diseased tissue or cell type is located in the body. The contrast imaging agent nanobubbles may also be used monitor how well a treatment is working by identifying any remaining diseased tissue or cell after treatment has been administered.

The nanobubble may be used for research purposes. Research purposes include imaging epigenetic changes within a cell, including changes to the number of methylated nucleic acids in the cell, and imaging changes to the DNA and histone organization. The nanobubbles may include fluorophores for imaging using an imaging device such as a spectrometer. Drug development assays may incorporate these nanobubbles to monitor changes within the cell given a particular small molecule. These assays include two dimensional (2D) and three dimensional (3D) culture techniques. The nanobubbles may be used to optimize drug delivery for certain agents which need to be protected prior to reaching the specific cell type or tissue type of interest.

Example 5 illustrating use of nanobubbles in research. The nanobubbles used were prepared as described in example 3. Different experimental set ups were utilized to best study the effects on nanobubble concentrations and treatment time on the target cells. Initial set up included a total treatment time of 48 hours with nanobubbles (0.5 mg/mL) being added at the start of incubation; after 24 hours of incubation; and both at the start and after 24 hours of incubation. A negative control was maintained in both normoxic and hypoxic environment which did not undergo any nanobubble treatment.

An experimental setup to measure the concentration dependence of the oxygenated nanobubble treatment upon the 5 mC methylation levels in HeLa cells cultured in hypoxic conditions is described. The experimental set up involved the addition of 500 uL of oxygenated nanobubbles (0.1 mg/mL, 0.5 mg/mL, and 1.0 mg/mL) to the experimental cells cultures. The treatment took place every 8 hours while the cells were incubated in the incubator with hypoxic conditions.

After a total incubation time of 48 hours, the cell cultures were washed with 1×PBS buffer (Gibco by Life Technologies) and detached from the flask with 0.25% 1× Trypsin-EDTA (Gibco by Life Technologies). DNA was extracted from all the samples using the DNeasy Blood and Tissue Kit (Qiagen).

All the experimental as well as the control cell cultures were run in duplicate so as to increase the overall accuracy of the treatment experiments.

All extracted DNA samples were quantified using Nano-Drop ND100 Spectrophotometer.

All DNA samples were diluted to 2 ng/μL with DI water. 100 μL of the diluted DNA from each experimental set up was added to individual wells in a 96-well plate with 100 uL of Reacti-Bind DNAcoating solution (Thermo Scientific). The plate was incubated at room temperature for 4 hours on a rocker agitator. After every incubation step, the wells were washed thrice with DI water.

After the first round of incubation and washing, 200 uL of 0.5% (w/v) Casein (Sigma Aldrich) prepared in PBS (10 mM PBS with 150 mM NaCl) was added with each well. Incubation at 37° C. was conducted for an hour. In order to globally tag the 5 mC sites, 100 uL of 0.5 ug/mL of the primary mouse monoclonal anti 5-Methyl-cytosine (5-mC) antibody (Epigentek Group Inc., Farmingdale, N.Y.) was added to each well. Incubation was carried at 37° C. for 2 hours. To tag the primary antibody, 100 uL of 1.0 ug/mL of the secondary antibody, goat anti-mouse IgG-Biotin conjugate (Pierce Thermo Fisher Scientific, Waltham, Mass.) was added to each well. Incubation was carried out at 37° C. for an hour. To form the HRP-streptavidin conjugate, 100 uL of 0.125 ug/mL of Pierce High sensitivity HRP-labelled streptavidin (Pierce Thermo Fisher Scientific, Waltham, Mass.) was added to each well. Final incubation was conducted at 37° C. The primary and the secondary anti body along with HRP-streptavidin were diluted in PBS (Life Technologies) containing 0.5% (w/v) Casein (Sigma Aldrich) and 0.1% (v/v) Tween 20 (Bio-Rad). In order to generate the color in the assay, each well received a final treatment of 100 uL of 1-Step™ Ultra TMB-ELISA (Pierce Thermo Fisher Scientific, Waltham, Mass.). After 15 minutes of mild agitation on the rocker, 50 μL of 2M $H_2SO_4$ was added to each well in order to stop the color generating reaction. Spectrophotometer readings were taken at 450 nm using the ELISA endpoint model available on the SoftMax Pro 5.2 software pack. Each assay was performed in triplicate in order to improve the accuracy of the measurements.

Example 6 illustrating a use of nanobbules in research. Pancreatic beta cell line MIN6 was cultured using cell culture media consisting of 25 mM glucose, 15% inactivated FBS, 1% penicillin/streptomycin, 2 mM glutamine, 100 μM 2ME, 15 mM HEPES and 5% CO2. Upon reaching confluency of ~80%, cells were trypsinized and encapsulated. For encapsulation, a 1% sodium carboxymethylcellulose solution was prepared. MIN6 cells were centrifuged and resuspended in PBS. Cells were added into the carboxymethylcellulose solution under gentle agitation. 0.1% aluminium chloride solution was added further to complete the encapsulation. Cells were washed in PBS at least 3 times and resuspended in MIN6 media. For scanning electron microscopy (SEM) imaging, cells were fixed in 2.5% glutaraldehyde and freeze dried before imaging.

Another application for the nanonbubbles is to measure intraocular pressure in glaucoma. Glaucoma has increased ocular pressure as a primary risk factor. Further, oxygen supply (through a hyperbaric chamber) has been proven to reduce intraocular pressure and has been utilized as a therapy conventionally. There are also several drugs available for reducing any intraocular pressure (IOP). In some embodiments, oxygen comprising nanobubbles may be embedded in a hydrogel which is implanted near the vitreous tumor of an eye or between the conjunctiva and the sclera or at an appropriate position in the eye where oxygen release can provide therapeutic relief or decrease in intraocular pressure. This will aid quantification of intraocular pressure using ultrasound by measuring parameters including or not limited to gray scale imaging intensity, volume of implant, length/dimensions of implant/device. Further, upon bursting the bubbles at a tuned frequency or power or intensity, there will be oxygen and/or drug is released to aid in reducing the symptoms of glaucoma. Thus, the method is minimally invasive, reduces discomfort, and combines diagnosis and quantification of intraocular pressure and glaucoma along with therapy.

Nanobubbles of said invention can be used to enhance ultrasound backscatter. One of the non-limiting examples of an application wherein the ultrasound backscatter signal enhancement can be used is velocimetry of vascular and opaque flows. Velocity vectors can be determined to indicate the flow within the field using particle image velocimetry (PIV) or echo-PIV. The said nanobubbles can also be used to increase the image spatial resolution. The applications of the said nanobubbles are echo-PIV for carotid vascular imaging, blood flow condition monitoring, vortex formation in heart valves, heart diseases, cardiovascular diseases, cardiovascular hemodynamics, and echocardiography.

Referring now to FIG. 26, which is an image of 200 nm nanobubbles showing significant optical scattering using dark field microscopy, said nanobubbles can also be used for signal enhancement in dark field microscopy or hyperspectral microscopy. Nanobubbles can be used to enhance optical scattering imaging and can be used as a tool for theragnostics. The nanobubble brightness, scattering, contrast, and signal enhancement can be tuned by changing the nanobubble properties including but not limited to size, shape, polymer layer thickness, ligands etc. It is also possible to obtain ultra-sharp spectra of the nanobubbles. Simultaneous excitation or nanobubble size specific excitation can be used to trigger the bubbles and obtain bursting of the nanobubbles using external energy source such as lasers, ultrasound etc.

The nanobubbles of said invention can also be used for ablation of cells, tissues, or organs using external energy source such as ultrasound, microwave, or lasers. Ablation can be due to collapse of the nanobubble structure and generation of a mechanical pressure wave. The applications of nanobubble cavitation or ablation are, including but not limited to, heart diseases, Alzheimers, brain diseases, cancer, diabetes, removal of arterial clogs etc.

Additional disclosure is found in Appendix-A, Appendix-B, and Appendix-C filed herewith, the entirety of each is incorporated herein by reference into the present disclosure.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A nanobubble composition at about 0.5 mg/ml to about 1 mg/ml for controlled ultrasound activated cargo release in targeted cells, wherein the ultrasound activated cargo release changes said cells' 5 mC level and gene expression pattern, wherein the nanobubble composition is made by:

providing a homogenized gel consisting of a cellulose based material at about 0.1% to about 2% w/v, saturating the homogenized gel with oxygen and optionally with cargos under continuous sonication to produce nanobubbles, cross-linking the homogenized gel, nanobubbles and cargos with a trivalent cross-linker at about 0.1% to about 1% to form an encapsulated structure, wherein said encapsulated structure comprises a continuous outer shell and an inner wall of the continuous outer shell, wherein the continuous outer shell and inner wall encapsulate cargos selected from the group consisting of fluorophore, a pharmaceutical, a biomolecule, a ligand, contrast imaging agents, antibodies, lipids, protein receptors, aptamers or combinations thereof; and a hollow core, wherein the hollow core is filled with oxygen, and wherein the nanobubble is less than about 250 nm in diameter.

2. The nanobubble of claim 1 wherein the cellulose based material comprises sodium carboxymethyl cellulose, polyethylene glycol, chitosan sodium hyaluronate, poly(lactic-co-glycolic acid, polystyrene, hydrogels, sodium starch glycolate, poly(vinyl pyrrolidone), microcrystalline cellulose, hydroxypropylmethyl cellulose, HPMC phthalate, oxycellulose, sodium stearyl fumarate, alpha cellulose, pre-gelatinized starch, starch acetate, albumin, dextran, chitosan or combination thereof.

3. The nanobubble of claim 1 wherein the nanobubble is less than about 200 nm in diameter.

4. The nanobubble of claim 1 wherein the nanobubble is less than about 100 nm in diameter.

5. The nanobubble of claim 1 wherein the nanobubble is less than about 50 nm in diameter.

6. The nanobubble of claim 1 wherein the nanobubble bursts at a frequency of about 1.1 MHz over a range of about 0.01 to about 1100 mv/cm$^3$.

7. The nanobubble of claim 6 wherein about 50 percent of the nanobubble will burst at 70 mv/cm$^3$.

8. The nanobubble of claim 1 wherein the hollow core and the outer shell have pores.

9. A method of controlled delivery of a cargo to a cell, comprising:

providing a nanobubble of claim 1 to the cell;

providing a form of energy at a given frequency or power or intensity of sound wave, wherein the form of energy is configured to trigger the nanobubble of claim 1 to resonate and burst releasing the cargo to the cell.

10. The method of claim 9 wherein the form of energy is adjusted to trigger the bursting time.

11. The method of claim 9 wherein the nanobubble size and density is adjustable, with the size between about 50 nm to about 200 nm and the density between about 0.5 mg/ml to about 1 mg/ml.

12. The nanobubble composition of claim 1, wherein the polymeric material is 0.1% w/v sodium carboxymethyl cellulose (NaCMC).

13. The nanobubble composition of claim 1, wherein the cross-linker is 1% aluminum chloride (AlCl$_3$).

* * * * *